(12) United States Patent
Thompson et al.

(10) Patent No.: US 9,448,174 B2
(45) Date of Patent: Sep. 20, 2016

(54) FLUOROMETRY

(71) Applicants: Edward John Thompson, Maidstone (GB); Ilan Tal, Haifa (IL)

(72) Inventors: Edward John Thompson, Maidstone (GB); Ilan Tal, Haifa (IL)

(73) Assignee: Attomole Ltd, Maidstone, Kent (GB)

( * ) Notice: Subject to any disclaimer, the term of this patent is extended or adjusted under 35 U.S.C. 154(b) by 0 days.

(21) Appl. No.: 14/221,305

(22) Filed: Jun. 16, 2014

(65) Prior Publication Data

US 2014/0308679 A1 Oct. 16, 2014

Related U.S. Application Data

(60) Provisional application No. 61/806,228, filed on Mar. 28, 2013.

(51) Int. Cl.
*G01N 21/64* (2006.01)

(52) U.S. Cl.
CPC ........ *G01N 21/6428* (2013.01); *G01N 21/645* (2013.01); *G01N 21/6408* (2013.01); *G01N 2021/6463* (2013.01)

(58) Field of Classification Search
CPC ............... G01N 21/6408; G01N 21/6458; G01N 21/6428; G02B 26/04
USPC ....... 250/233, 236, 351; 422/82.08; 436/172
See application file for complete search history.

(56) References Cited

U.S. PATENT DOCUMENTS

| | | | | |
|---|---|---|---|---|
| 4,954,714 A | * | 9/1990 | Pollak ................ | G01N 21/6408 250/458.1 |
| 6,839,134 B2 | * | 1/2005 | Saito .......................... | G01J 3/08 250/458.1 |
| 2008/0003668 A1 | * | 1/2008 | Uchiyama .............. | G01N 21/07 435/287.2 |
| 2009/0232486 A1 | * | 9/2009 | Sato ................... | G01N 21/6452 396/200 |
| 2011/0057119 A1 | * | 3/2011 | Connally ........... | G01N 21/6408 250/459.1 |

* cited by examiner

*Primary Examiner* — Erik B Crawford
(74) *Attorney, Agent, or Firm* — Maxey Law Offices, PLLC; Stephen Lewellyn

(57) ABSTRACT

The invention relates to fluorometry, and in particular to methods and apparatus for time-delayed detection of fluorescence in a sample, for example for use in a clinical setting. Exemplary embodiments disclosed relate to a fluorometer (100) comprising a light source (101), a light detector (102), a sample holder (103) disposed between the light source and light detector, a motor (104); and a light transmission modulator (105) disposed around the sample holder and comprising a pair of plates (106, 107) attached to the motor for rotation about a common axis (108), the pair of plates arranged to allow transmission from the source to the sample in a first rotated position, to allow transmission from the sample to the detector in a second rotated position and to block direct light transmission between the source and detector in both first and second rotated positions.

11 Claims, 11 Drawing Sheets

FLUOROMETRY

The invention relates to fluorometry, and in particular to methods and apparatus for time-delayed detection of fluorescence in a sample, for example for use in a clinical setting.

Techniques using fluorescence can be employed for detection of biomolecules. Various techniques are known relating to detection of fluorescence in this way, as for example disclosed by Connally et al., in "High Intensity Solid-State UV Source for Time-Gated Luminescence Microscopy", Cytometry Part A 69A: 1020-1027, 2006, in which a UV LED based system for the detection of fluorescence in probes comprising lanthanide chelates is described. Such fluorescent probes have long fluorescence lifetimes, which enables their detection to be distinguished from background fluorescence having much shorter lifetimes. In general, in order to distinguish probe fluorescence from background fluorescence, a light signal can be detected from a sample over an acquisition period that begins once the background fluorescence has effectively disappeared.

In Connally et al., an optical arrangement is used employing an electronically triggered UV LED and camera, the camera being triggered after a hold-off period following a falling edge of an excitation signal provided to the LED. Earlier time-gated instruments are also mentioned, in which chopper wheels are employed as inexpensive pulsed excitation sources. Such earlier instruments are mentioned by Connally et al. as being disadvantageous due to pulse profiles having slow rising and falling edges and having limits on resolution and sensitivity. Other apparent limitations of chopper wheels include the inflexible nature of the pulse regime, the inefficient use of light energy and the risk of image blur arising from drive motor vibration. Noise and inadequate sensitivity are particular problems when the concentration of the fluorescent probe is low, for example, when it is used to detect biomolecules at low abundance in clinical samples.

An example of a mechanically-gated fluorometer using a chopper wheel is disclosed by Greinert et al., in "E-Type Delayed Fluorescence Depolarization, A Technique to Probe Rotational Motion in the Microsecond Range", Journal of Biochemical and Biophysical Methods, 1 (1979) 77-83, in which a pulsed nitrogen laser is used to illuminate a sample and a chopper wheel is used to block the early fluorescence emission and allow a delayed portion through to a photomultiplier. A further example is disclosed by Marriott et al., in "Time resolved imaging microscopy", Biophys. J Vol. 60 December 1991 pp 1374-1387, in which two phase-locked choppers and a slow-scan CCD camera are attached to a fluorescence microscope, a sample being illuminated by a periodic train of light pulses and an image recorded within a defined interval after the end of each excitation period.

A further example of a mechanically-gated fluorometer is disclosed in U.S. Pat. No. 4,954,714, in which a chopper device is used in conjunction with a camera, the chopper preventing exposure of photographic film to background fluorescence and coordinating with the rate of flashing of a light source to ensure that the film is only exposed to time-delayed fluorescent radiation.

A problem with existing mechanically-gated fluorometer systems is, as stated by Connally et al., that of slow rising and falling pulse edges, which can make detection of fluorescent probes having short lifetimes more difficult. A further problem relates to the size and complexity of the apparatus needed to incorporate the mechanical components and lens systems in a fluorometer system, which may prevent such a system from being used in settings other than in a controlled laboratory, for example in a clinical environment such as a hospital bedside setting where space is more limited. Operation of such machines may also be complicated, and require an expert or highly skilled operator. Various tests may be required to ensure reliability and satisfy quality control requirements. As a consequence of these problems, clinical samples are typically removed to a laboratory for analysis, and the results of analysis may be obtained too late to inform clinical decision making, particularly in critical care.

A further problem relates to the use of complicated systems, whether mechanical or electrical/electronic, for synchronising light emitted by a light source with light detected by a detector (or, in the case of U.S. Pat. No. 4,954,714, a photographic film) so that only the time-delayed fluorescence is detected. This problem is to some extent addressed in U.S. Pat. No. '714 by combining a chopper for light emission with a chopper for light detection into a common chopper wheel, although this only partly addresses the problem of the size of the apparatus used, and does not address (and may possibly accentuate) problems relating to motor vibrations causing image blur, or in cases where an electronic light sensor is used, possible electrical noise from the motor affecting the light detector.

In "Fluorescence and Phosphorescence", Praktikum VPII Fluoresenz, 27 Mar. 2006, XP55019671 and in JP 49 089587 A, a fluorometer is disclosed having a light source, a light detector, a sample disposed between the light source and light detector, and a light transmission modulator disposed around the sample holder comprising a pair of plates arranged for rotation about a common axis, the plates arranged to allow transmission from the light source to the sample in a first rotated position, to allow transmission from the sample to the detector in a second rotated position and to block direct light transmission between the light source and light detector in both first and second rotated positions.

It is an object of the invention to address one or more of the above mentioned problems. The listing or discussion of an apparently prior-published document in this specification should not necessarily be taken as an acknowledgement that the document is part of the state of the art or is common general knowledge.

In accordance with the invention as defined by the appended claims, there is provided a time-resolved fluorescence system, a method of detecting time-resolved fluorescence of a sample, and a computer program for instructing a computer system of the time-resolved fluorescence system to perform a method of detecting time-resolved fluorescence in a sample.

Disclosed herein is a fluorometer comprising:
a light source;
a light detector;
a sample holder disposed between the light source and light detector;
a motor; and
a light transmission modulator disposed around the sample holder and comprising a pair of plates attached to the motor for rotation about a common axis, the pair of plates arranged to allow light transmission from the light source to the sample in a first rotated position, to allow light transmission from the sample to the light detector in a second rotated position and to block direct light transmission between the light source and light detector in both first and second rotated positions.

An advantage of the light transmission modulator being disposed around the sample holder between the source and detector and comprising a pair of plates attached for rotation about a common axis is that the overall size and complexity of the apparatus can be reduced compared to existing systems. The phase relationship between light transmission and detection is determined by the relative rotational positions of the pair of plates, rather than by a more complicated synchronisation between separate chopper wheels or between a light source and a single chopper wheel as disclosed in the prior art noted above. The apparatus is therefore more suitable for use in situations other than in a controlled laboratory environment, and can be more readily set up for use by non-expert operators.

Using a single motor to drive both plates of the modulator allows for the modulator to be kept in synchrony regardless of the position or speed of rotation of the modulator. The motor can also be positioned away from the light detector, thereby reducing the effect of any noise, whether electrical or mechanical, on the detector.

The light source and light detector are preferably electronic devices, the source being for example a light emitting diode or laser and the detector being a light sensor such as a charge-coupled device or other type of semiconductor-based light sensor.

For initiating fluorescence in a sample held in the sample holder, the light source is preferably able to emit ultra violet (UV) radiation, while the light detector will generally be able to detect fluorescence in the visible band.

The pair of plates of the light transmission modulator may be configured as plates extending orthogonally either side of the sample holder from a common rotating axle. Each plate may comprise a light transmission portion over a first subtended angle and a light blocking portion over a second subtended angle of the plate. The light blocking portions of the plates preferably overlap each other to block direct transmission of light from the source to the detector at any rotated position. The plates may have a fixed relative rotational position, although this position may be adjustable by altering the rotational position of one or both of the plates with respect to the other, for example to adjust the relative timing of the light blocking and transmission portions of each plate when rotating at a selected speed.

The plates may in certain embodiments comprise substantially semicircular, or half-moon, shapes, such that the light transmission and blocking portions are roughly equal. In certain embodiments, the light blocking portions may have a greater subtended angle than the light transmission portions, allowing an overlap that determines a time delay between when light transmission from the source is cut off from the sample and detection of light from the sample to the detector is enabled. This also reduces the amount of leakage of light from the source to the detector.

The light source may be configured to be controlled such that its operation is synchronised with the rotational position of the light transmission modulator, or may be operated continuously during a measurement sequence, relying only on the modulator to block transmission during each fluorescence measurement period.

Also disclosed herein is a method of detecting time-resolved fluorescence of a sample, the method comprising the steps of:
  providing a fluorometer according to the above described apparatus;
  disposing the sample in the sample holder;
  operating the motor to rotate the light transmission modulator;
  operating the light source to illuminate the sample when the light transmission modulator is in the first rotated position; and
  capturing light signal data from the light detector indicative of fluorescence of the sample.

An advantage of the method is that measurements can be carried out using an apparatus having a reduced size and complexity compared to previous known apparatus.

The method according to the invention comprises the step of stopping operation of the motor, wherein the step of capturing light signal data is carried out after stopping operation of the motor and while the light transmission modulator is rotating. An advantage of stopping operation of the motor before capturing light signal data from the light detector is that electrical noise and mechanical vibrations from the motor are reduced or eliminated. Typically a measurement can be quite adequately carried out for a period of time after the motor has been switched off, or disengaged, before the rotational speed of the light modulator has reduced to an extent where time-delayed fluorescence is no longer captured.

The method may comprise the step of detecting a rotational position of the light transmission modulator from a signal provided by a rotational detector and capturing trigger signals from the rotational detector for synchronising the captured light signal data with the rotational position of the light transmission modulator. An advantage of detecting the rotational position of the modulator is that measurement of the time-delayed fluorescence can be synchronised with a known position of the modulator, allowing a trigger signal from the rotational detector to be used to determine the point where transmission from the light source is cut off.

Suitably, a measure of fluorescence in the sample is determined by extracting a plurality of decay curves from the captured light signal data and deriving an average output signal from the plurality of decay curves, a starting point of each decay curve being determined according to the position of a corresponding trigger signal. The signal to noise ratio for each individual measurement may be low. Deriving an average output signal from a number of successive measurements taken on the same sample can increase the overall signal to noise ratio of the measurement.

Also disclosed herein is a time-resolved fluorescence system comprising:
  a fluorometer according to the above described apparatus; and
  a computer system connected to the controller, the light source and the light detector,
  wherein the computer system is configured to operate the motor to rotate the light transmission modulator, operate the light source to illuminate the sample when the light transmission modulator is in the first rotated position and capture light signal data from the light detector indicative of fluorescence of the sample.

The general advantages of the system are that a smaller and less complex system is enabled.

The computer system according to the invention is configured to stop operation of the motor once the light transmission modulator is rotating and to capture light signal data from the light detector after stopping operation of the motor and while the light transmission modulator is rotating. As mentioned above, an advantage of stopping the motor before signal acquisition is that of reduced electrical noise and vibration, which can otherwise adversely affect the light signal measurements.

The system may comprise a rotation detector connected to the computer system and configured to detect a rotational position of the light transmission modulator, wherein the computer system is configured to capture signals from the rotation detector and to synchronise the captured light signal data with signals from the rotation detector. As mentioned above in connection with the second aspect, detecting the rotational position of the modulator allows for synchronisation of the rotational position of the modulator with signals captured from the light detector. This is particularly advantageous when the system is configured to capture light signal data after stopping operation of the motor, because the change of rotation speed of the modulator can be accounted for during signal acquisition and analysis.

Also disclosed herein is a computer program for instructing a computer system as described above to perform a method of detecting time-resolved fluorescence in a sample disposed in the sample holder of the apparatus, the method comprising the steps of:

operating the motor to rotate the light transmission modulator;

operating the light source to illuminate the sample when the light transmission modulator is in the first rotated position;

capturing light signal data from the light detector indicative of fluorescence of the sample; and acquiring trigger signals from a light sensor configured to detect light transmission from the light source to the sample, wherein the steps of operating the light source and capturing light signal data are carried out after stopping operation of the motor and while the light transmission modulator is rotating.

The computer program is preferably provided on a computer-readable storage medium such as a memory or a disc suitable for installation on a computer system according to the third aspect of the invention.

Suitably, according to the above-described method, the sample comprises an amount of a fluorescent molecule or moiety which is indicative of the amount of a selected biological molecule present in a specimen. Competitive and non-competitive assay methods for quantitative detection of biological molecules, for example immunoassays such as enzyme-linked immunosorbent assays (ELISA) or other capture assays are well known in the art (e.g. Green and Thompson (1997) J Immunol Methods 205:35-41).

The sample may be prepared by:

(i) contacting a specimen with a capture molecule, such as an antibody, which is capable of binding specifically to the selected biological molecule to form a complex between the capture molecule and the selected biological molecule;

(ii) detecting the complex in a non-competitive or competitive assay by contacting the complex, the capture molecule or the selected biological molecule directly or indirectly with a probe comprising a moiety which is capable of participating in fluorescence, such as a lanthanide chelate, wherein the amount of the probe is indicative of the amount of the selected biological molecule present in the specimen; and (iii) exposing a test sample comprising the probe to conditions in which fluorescence is emitted.

Assays such as immunoassays can be competitive or noncompetitive. In a typical competitive immunoassay, a labeled biological molecule competes with the biological molecule in the sample for a capture molecule e.g. antibody which binds specifically to the biological molecule. The amount of labeled biological molecule bound to the capture molecule is then measured. There is an inverse relationship between concentration of biological molecule in the sample and the quantity of labeled biological molecule detected. In noncompetitive assays, including immunoassays, the biological molecule in the sample is bound to a capture molecule e.g. antibody, then a labeled detection reagent, typically an antibody, is bound to the biological molecule. The amount of labeled detection reagent bound to the biological molecule is then measured. Unlike the competitive method, the results of the noncompetitive method will be directly proportional to the concentration of the biological molecule. Typically the labeled detection reagent binds to a different epitope than the capture molecule.

In a competitive assay, the labeled biological molecule is bound directly to the capture molecule. In a noncompetitive assay, the labeled detection reagent is bound directly to the biological molecule. Either labeled biological molecule or labeled detection reagent may be a probe comprising a moiety which is capable of participating in fluorescence. Alternatively, either such labeled molecule may be bound by a further reagent before the probe is added. In that case, the biological molecule or capture molecule is bound indirectly by the probe.

Typically, in either type of assay, the capture molecule is adsorbed on or conjugated to a solid substrate, such as magnetic beads. After the specimen is added and the biological molecule binds to the capture antibody, non-bound materials are typically removed by washing. The test sample to be subjected to fluorescence detection therefore typically comprises the probe and bound materials that are not removed by washing.

Suitable fluorescent molecules or moieties included lanthanide chelates. Suitable lanthanide ions are terbium, europium, samarium and dysprosium. Typical chelates comprise a lanthanide chelator covalently joined to a sensitizer, which captures light. Suitable chelators, sensitizers and lanthanide chelates are described in U.S. Pat. No. 5,639,615 (Selvin and Hearst; Regents of the University of California). Suitable methods of coupling the chelates to various compounds to create probes are also disclosed. U.S. Pat. No. 4,808,541 (Wallac Oy) describes fluorescent lanthanide chelates in which the chelating group is diethylenetriaminepentaacetic acid (DTPA) or a derivative thereof. US 2010/0036102 (Wallac Oy) describes lanthanide chelates in which a chromophoric moiety (sensitizer) comprises one or more trialkoxyphenyl pyridyl groups and a chelating moiety may comprise carboxylic acid groups.

A preferred lanthanide chelate may be made according to a modification of the method of Bailey et al (1984) Analyst 109: 1449-1450. Bailey describes the synthesis of a lanthanide chelate in which DTPA is the chelator and 4-aminosalicylic acid (pAS) is the sensitizer. In essence, pAS dried and dissolved in DMSO is added drop-wise to DTPAA (the biscyclic anhydride of DTPA) and triethylamine dissolved in DMSO, to form the DTPA-pAS derivative. A conjugate of the chelate is prepared by mixing the DTPA-pAS derivative with a solution of a protein (in this case human serum albumin) in a solution (in this case 0.1 M phosphate buffer). Bailey describes purification of the conjugate from excess label by dialysis. However, it is preferred to avoid the dialysis step but rather to filter the product, for example using a 0.2 micron filter. The latter procedure provides for a probe which has a much greater stability of fluorescence than the probe described by Bailey. Further variations to the method are possible. For example, the conjugate may contain polylysine rather than a protein. If a protein is used, it may be gelatin. The solution may contain a buffer other than phosphate buffer. The conjugate may be biotinylated and used, for example, in an indirect detection method by binding to a biotinylated antibody via an avidin molecule.

Suitable fluorescent molecules or moieties, such as the above-mentioned lanthanide chelates are typically fluorescent in typical buffers and assay conditions. Other reagents need to be subjected to enhancement solutions to generate fluorescence, such as in the DELFIA system from Perkin Elmer Life Sciences. In that case, the probe comprising a moiety which is capable of participating in fluorescence is typically a weakly chelated europium ion. Under appropriate conditions, the europium ion dissociates and forms a new highly fluorescent chelate.

Suitably, the specimen from which the sample to be tested is prepared is a patient sample, such as a sample of urine, blood, serum, plasma or cerebrospinal fluid (CSF). The type of patient sample may depend on the patient's condition and the information that the clinician needs to inform clinical decision making. Suitable biological molecules which may be detected in a patient sample include proteins or glycoproteins, particularly tissue-specific proteins or glycoproteins. Suitable examples are S-100 proteins such as S-100b (Green and Thompson, supra), which is expressed by astrocytes; glial fibrillary acidic protein (GFAP), which is expressed by astrocytes; neuron-specific enolase (Schaarschmidt et al (1994) Stroke 25: 558-565) which is expressed by neurons; neurofilaments NFheavy and NFlight which are expressed by neurons; and ubiquitin carboxyl-terminal esterase L1 (UCHL1)
which is expressed by neurons. Suitable heart proteins include TnI and TnT troponin expressed by heart muscle, N-Terminal-pro-Brain-derived-Natriuretic-peptide (NT-proBdNP) and creatine kinase MB protein (CKMB). Suitable kidney proteins include beta 2 microglobulin. Suitable liver or gut proteins include carcinoembryonic antigen (CEA). A suitable lung (infection) protein is C reactive protein (CRP), which is indicative of acute inflammation. For patients who develop deep vein thrombosis, it may be useful to determine fibrinogen D-dimer.

The presence of brain proteins in biological fluids, particularly blood and its derivatives, is of clinical concern as it suggests release of brain proteins into the CSF, blood or urine. This may be a consequence of brain trauma caused by stroke, acute injury or other conditions. S-100b is a protein found predominantly in the central nervous system, and its presence in CSF is associated with acute neurological damage (Green and Thompson, supra). Schaarschmidt et al supra, assayed neuron-specific enolase retrospectively in patients suffering cerebrovascular diseases. The trajectory of data points from any given patient can show either increase, decrease, or no change, as well as the "speed" or slope of any changes. This gives useful information about the diagnosis and/or treatment of individual patients, and may be used in conjunction with other information, such as the age, sex, weight, etc. of the patient. Timofeev and Hutchinson (2006) Injury, Int J Care Injured 37: 1125-1132) shows how it might be necessary to perform decompressive craniectomy if the brain swells up due to cerebral oedema. Subramaniam and Hill (2009) The Neurologist 15: 178-184 stresses the need for more information in conjunction with MRI and CT scans to decide on whether or when to apply decompressive craniectomy. Biochemical analyses may also be important during surgery when the anesthetised patient obviously cannot report on pain or paralysis of limbs.

Also disclosed herein is a method of clinical evaluation of at least one patient sample comprising:

(i) collecting at least one patient sample, such as a sample of urine, blood, serum, plasma or cerebrospinal fluid;

(ii) contacting the at least one patient sample with a capture molecule, such as an antibody, which is capable of binding specifically to a selected biological molecule to form a complex between the capture molecule and the selected biological molecule;

(iii) detecting the complex in a non-competitive or competitive assay by contacting the complex, the capture molecule or the selected biological molecule directly or indirectly with a probe comprising a moiety which is capable of participating in fluorescence, such as a lanthanide chelate, wherein the amount of the probe is indicative of the amount of the selected biological molecule present in the at least one patient sample;

(iv) exposing at least one test sample comprising the probe to conditions in which fluorescence is emitted;

(v) detecting the time-resolved fluorescence of the at least one test sample according to the method described above; and (vi) estimating the amount of the selected biological molecule present in the at least one patient sample from the time-resolved fluorescence detected in the at least one test sample.

Methods of forming and detecting a complex between a biological molecule and a capture molecule are as discussed above. As noted above, in typical non-competitive assays, a linear relationship between the measured fluorescence and biological molecule concentration is assumed. For example, if sample A has double the optical density of sample B in the assay (background having been subtracted from both), it is assumed that the concentration of biological molecule is double in A compared to B. However, it is preferable to construct a standard curve of serial dilutions of known biological molecule concentration. By doing this, any variation from the linear relationship may be taken into account in estimating the quantity of the biological molecule in the sample.

Suitably, the method comprises obtaining multiple patient samples at intervals from a patient and estimating the amount of one or more selected biological molecules in the patient samples in real time. Suitable time intervals may be every 24 hours, every 12 hours, every 6 hours, every 4 hours, every 2 hours, every hour or two, three, four or six times per hour. The frequency of the sample collection and testing will depend on clinical need. Testing may go on for hours, days, weeks or months. The method may also further comprise diagnosing or prognosing the patient or modifying the patient's treatment depending on the presence, amount and/or a change in the presence or amount over time of the one or more selected biological molecules in the patient sample or samples.

Other optional and advantageous features of the various aspects of the invention may be found in the following detailed description of embodiments of the invention.

Aspects and embodiments of the invention are described in further detail below by way of example and with reference to the enclosed drawings in which.

Figure 16:
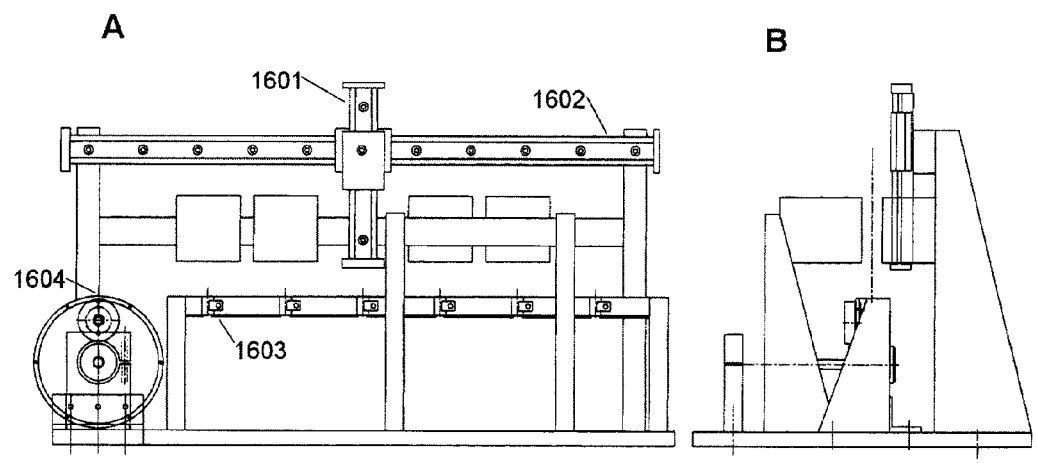
Figure 17:
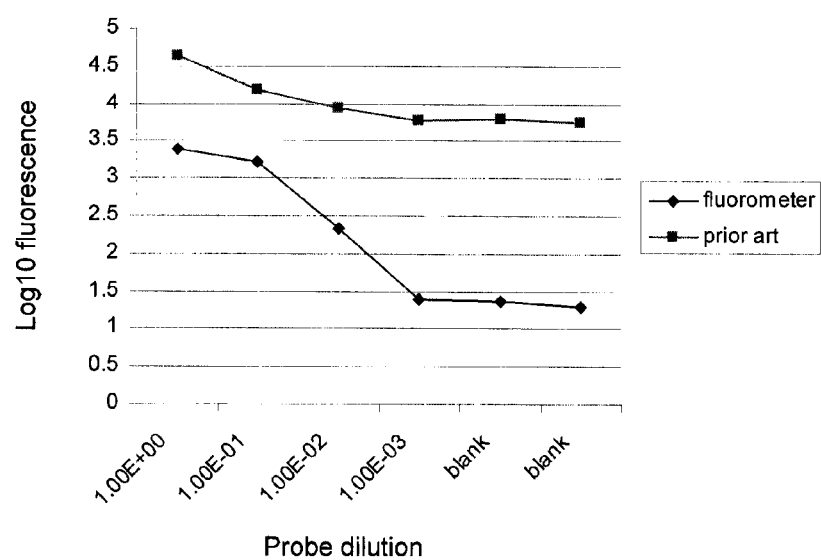

FIGS. 16a and b are schematic front and side views respectively of an exemplary fluorometer; and FIG. 17 is a plot of $\log_{10}$ fluorescence versus probe concentration obtained using a fluorometer as described herein and a fluorometer of the prior art.

FIG. 1 shows a schematic representation of the main components of an exemplary fluorometer 100. The fluorometer 100 comprises a light source 101 and a light detector 102 positioned either side of a light transmission modulator 105. The light transmission modulator 105 comprises a pair of plates 106, 107 either side of a sample holder 103 disposed between the source 101 and detector 102. The plates 106, 107 are mounted for rotation about a common axis 108 and are driven by a motor 104 attached to one end of a drive rod 109. An opposing end of the drive rod 109 is rotatably mounted in a bearing 110. Rotation of the modulator 105 causes light from the source 101 to the sample holder 103 to be alternately transmitted and blocked in sequence with a light transmission path from the sample holder 103 to the detector 102.

The plates 106, 107 in the illustrated embodiment of FIG. 1 are in the form of semicircular discs mounted in opposition on the drive rod 109 so that when light from the source 101 is being transmitted to a sample 111 held in the sample holder 103, a light transmission path from the sample 111 to the detector 102 is blocked by the second plate 107, and when the light transmission path from the sample 111 to the detector 102 is open, a light transmission path from the source 101 to the sample 111 is blocked by the first plate. Preferably, the first and second plates 105, 106 are partially overlapping so that a direct transmission path between the light source 101 and the light detector 102 is always blocked by one or both plates 106, 107. The degree of overlap between the plates determines the time delay between when the light transmission path 112 between the source 101 and sample 111 is blocked and the light transmission path 113 between the sample 111 and detector 102 is opened. This time delay is further determined by the speed of rotation of the modulator 105. As the speed of rotation is increased, this time delay is reduced. If the leading and trailing radial edges of the plates 106, 107 lie on a radial line extending from the axis, the radial position of the transmission paths 112, 113 relative to the axis 108 has no effect on the time delay.

Figure 1A:
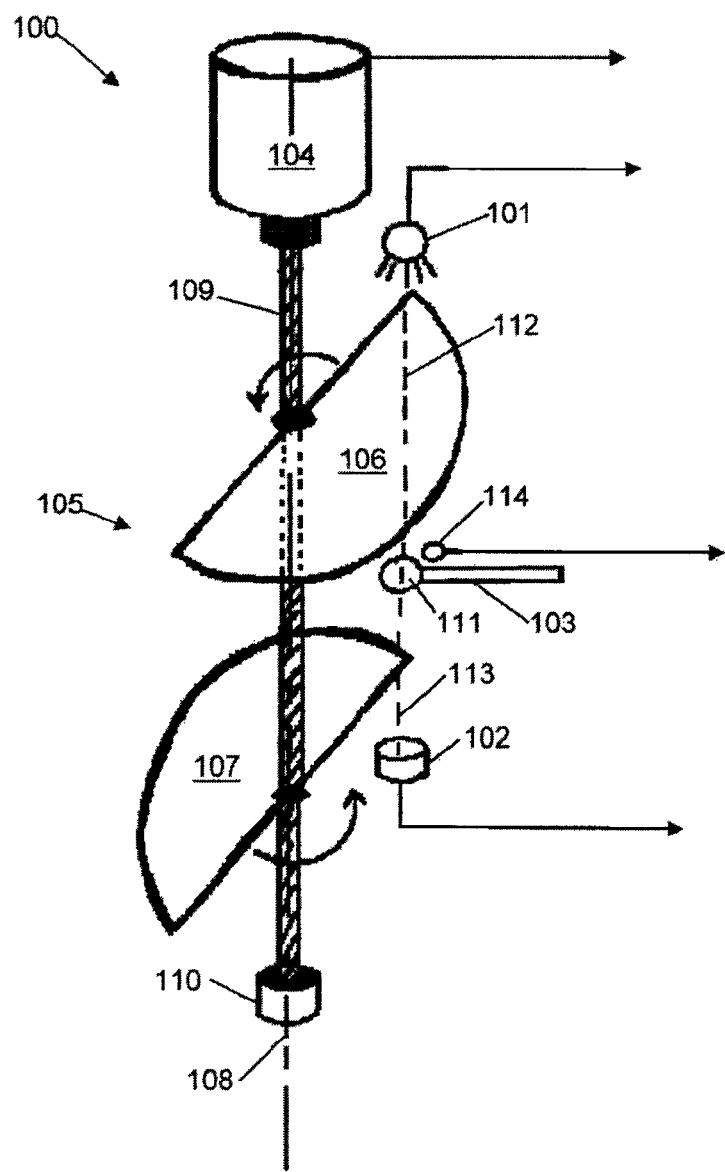
FIG. 1a is a schematic perspective drawing of an exemplary fluorometer.
Figure 1B:
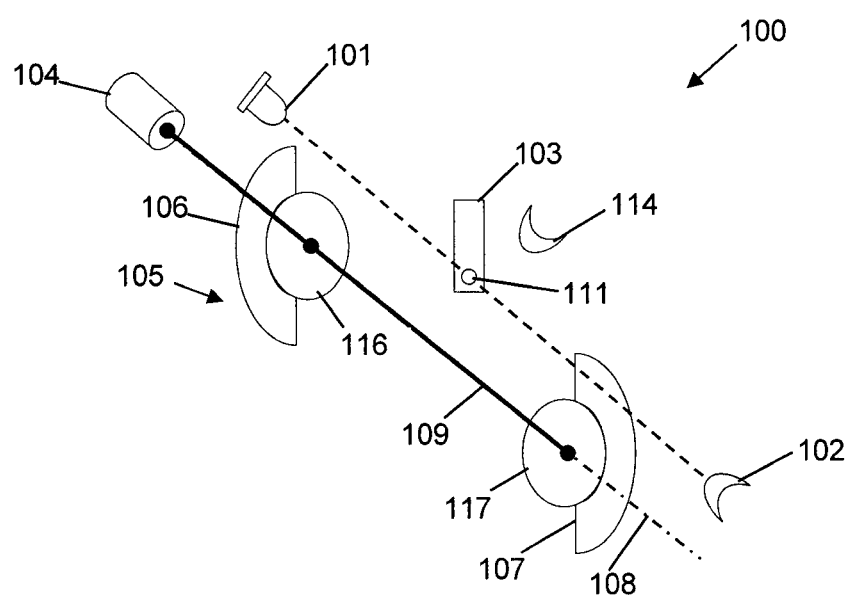
FIG. 1b is an alternative schematic perspective drawing of an exemplary fluorometer.

FIG. 1b shows an alternative representation of a fluorometer 100, in which corresponding reference numbers indicate the same components as described above for FIG. 1a. As with FIG. 1a, the representation is not to scale. In exemplary embodiments, the outer diameter of each of the plates 106, 107 may typically be around 130 mm, while an inner semicircular portion 116, 117 of each plate may be only a few millimeters smaller, for example around 122 mm in diameter. This small difference is sufficient to allow the required sequence of light transmission between the source 101 and detector 102. Maintaining a small difference between the diameters of the outer and inner portions of the plates 106, 107 reduces any imbalance along the shaft 109 while the plates are rotating at high speed. The plates 106, 107 may be further balanced by differentially weighting the inner and outer portions of the plates 106, 107 so as to ensure that the plates rotate with a minimum of imbalance. For example, the inner portion of each plate may comprise a weighted portion that results in the inner portion having the same rotational inertia as the outer portion. The plates 106, 107 are also preferably close together along the drive rod 109 to further minimise vibration. In an exemplary embodiment, the plates 106, 107 are spaced approximately 15 mm apart along the drive rod.

Figure 2A:
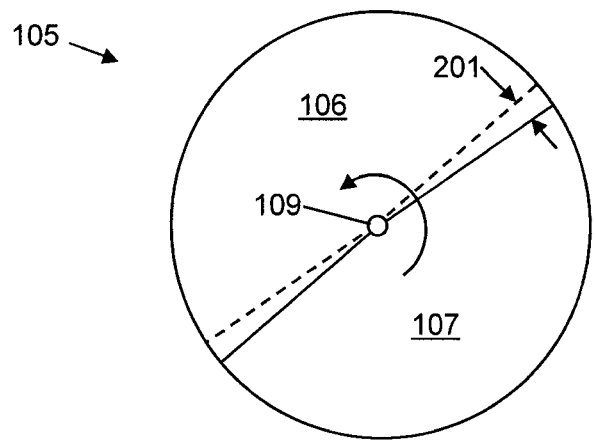
FIG. 2a is a schematic plan view of a light transmission modulator for the fluorometer of FIG. 1a or 1b.

FIG. 2a shows a plan view of the light transmission modulator 105 of FIG. 1, in which an overlap 201 is provided between the first and second plates 106, 107 to provide for a time delay between blocking the transmission path 112 from the source 101 to the sample 111 and opening the transmission path 113 from the sample 111 to the detector 102. This can be achieved by making the first or second plate in the form of a solid arc subtending an angle greater than 180 degrees rather than being semicircular.

Figure 2B:
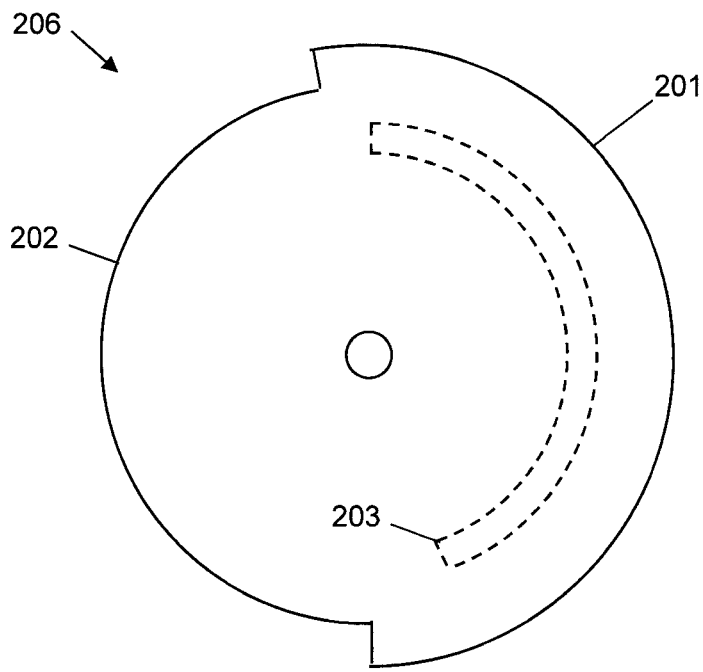
FIG. 2b is a schematic plan view of an alternative form of plate for use as a light modulator for the fluorometer of FIG. 1a or 1b.

FIG. 2b shows an exemplary plate 206 for use in place of either or both of the plates 106, 107 of the fluorometer 100 shown in FIGS. 1a and 1b. The outer diameter portion 201, which acts to block light to or from the sample 111 is only a few percent larger than the inner diameter portion 202, thereby reducing any vibrations due to imbalances. As an alternative, an arcuate slit 203 could be provided in the plate 206 configured to allow light to pass to or from the sample, thereby allowing the plate 206 to be balanced without the use of additional weights. The plate 206 can be designed such that the material removed to form the slit 203 can be closely or exactly balanced by the additional material forming the outer portion 201 of the plate 206.

An exemplary measurement cycle may take 20 ms in total, over which time the plates 106, 107 will rotate 360 degrees, or one full cycle. During a first 10 ms half of the cycle, UV light from the light source 101 is transmitted to a sample 111 in the sample holder 103, and transmission from the sample 111 to the detector is blocked by the second plate 106. The UV light excites the sample, together with any fluorescent probe within the sample 111. In the second 10 ms half of the cycle, the first plate 106 blocks light from the source and the second plate 107 allows fluorescence emitted by the sample 111 to be detected by the detector 102.

To achieve a measurement cycle of 20 ms, the motor 104 spins the plates 106, 107 at 3000 rpm, or 50 cycles per second. The motor 104 is preferably configured to operate at speeds of up to at least 10,000 rpm, or 167 cycles per second, at which speed a measurement cycle of 6 ms will be achieved. Higher speeds may be possible in order to reduce the measurement cycle further. Alternatively, or additionally, the modulator plates 106, 107 may each comprise two or more solid arc portions separated by light transmission portions, which will allow more than one measurement cycle per rotation. Using two or more arc portions has a further advantage of allowing the plates to be inherently mechanically balanced, thereby reducing vibration during a measurement cycle.

In an exemplary embodiment, the light source may be provided in the form of an ultraviolet light emitting diode (UV LED) having a wavelength of 310 nm with lens configured to provide a collimated beam, such as a UVTOP310-BL-T039 LED available from Roithner-Lasertechnik, Vienna (www.Roithner-Laser.com). A detector may be in the form of a photomultiplier light detector sensitive to wavelengths in the region of 300-700 nm, such as the H6780-1 available from Hamamatsu Photonics (www.hamamatsu.com). A secondary light sensor or trigger may be in the form of a silicon photodiode with pre-amplifier such as the S9269, also available from Hamamatsu Photonics. A suitable motor able to operate at the required speed in the region of 2000 to 3000 rpm may be provided by a Dremel drill, model 300 (www.dremel.com).

The fluorometer 100 may also incorporate a further light sensor 114 positioned close to the sample holder 103, to function as a rotation detector. The light sensor 114 is preferably positioned to receive light from the source 101 at the same time as the sample 111, for example by being positioned on a radial line extending between the axis 108 and the sample 111. An output signal from the light sensor 114 can therefore be used to provide a trigger signal for capturing data from the detector 102. Alternative means of detecting rotation of the modulator 105 may also be possible, for example by detection of the rotational position of the motor 104 or drive rod 109 using, for example, an optical encoder attached to the axle 109 or incorporated into the motor 104.

Figure 3:
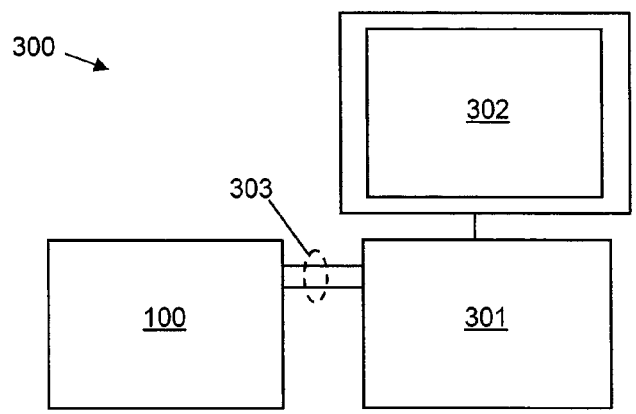
FIG. 3 is a schematic block diagram of a time-resolved fluorescence system according to an embodiment of the invention.

FIG. 3 shows a schematic block diagram of a time-resolved fluorescence system 300 according to an embodiment of the invention. The system 300 comprises a fluorometer 100 as described above and a computer system 301 connected to the fluorometer 100. The system 300 may also comprise a monitor 302 connected to the computer system 301 for displaying results and controlling operation of the computer system 301. The computer system 301 is connected to the fluorometer by connections 303 to allow for control and operation of, and/or receiving signal data from, the motor, light source, light detector and rotation detector in the fluorometer 100. The computer system 301 is configured to capture signals from the rotation detector, for example in the form of the light sensor 114 described above, and to synchronise signals received from the rotation detector with captured light signal data from the light detector 102.

Figure 4:
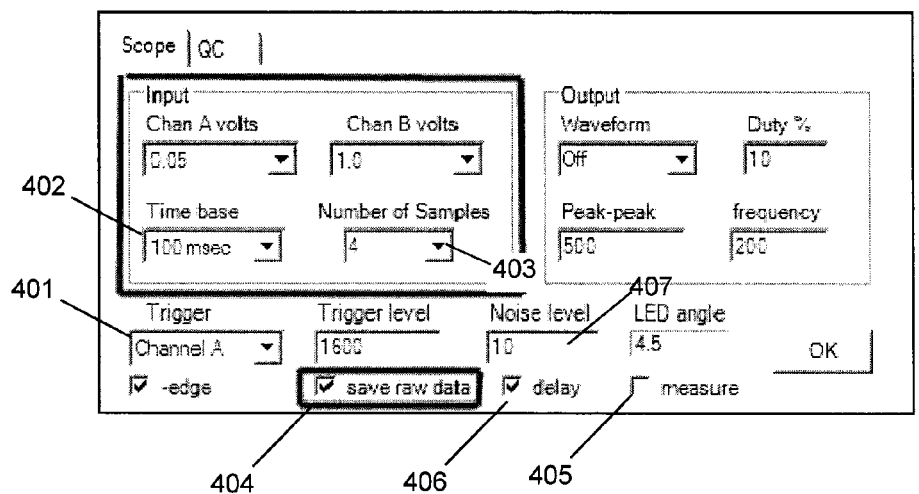
FIG. 4 is a screenshot of a portion of a display for configuring an oscilloscope function.

The computer system 301 may be configured in the form of an oscilloscope, in which signals received from the light detector 102 and the light sensor rotation detector 114 are used as channel inputs to the oscilloscope. An exemplary oscilloscope is the DSC2200C with EasyScope software, available from www.USB-Instruments.com, although other software- or hardware-based oscilloscopes will be able to perform the required functions. FIG. 4 illustrates a portion of a display for configuring this oscilloscope function. Using two light detectors, one signal is used as a trigger and the other is used to detect the delayed decay photons corresponding to fluorescence of a probe in the sample 111. The trigger signal measures the output from the light sensor 114 to measure photons activating the sample 111, which in the following example is assumed to be Channel A. The trigger pull down box 401 is therefore set to Channel A. The output signal from the photomultiplier (light detector) measuring the delayed fluorescence is set to Channel B. The time base 402 determines the length of the scan. The scan length should be long enough to capture several rotations of the modulator. In practice, a scan of 100 msec has been found to be sufficient for typical uses. The selected number of samples 403 is the number of times a given run will be sampled. Since the modulator will be slowing down during a scan (after the motor is turned off or disengaged from the modulator) this is a compromise to pick the best data range while the modulator is still turning at an acceptable speed. With a number of samples set to 4 and a time base of 100, this results in a total scan time of approximately 4*100=400 msec.

If the save raw data selection box 404 is used, the signal data from channels A and B will be saved, along with the time base 402 and number of samples 403. This allows for off-line analysis of the data after the original data are saved. The trigger signal and trigger level need not be saved, since these are used during acquisition and will determine how the data are acquired. Once the saved data have passed the acquisition stage a different analysis on the same original, acquired data may be carried out.

Figure 5:
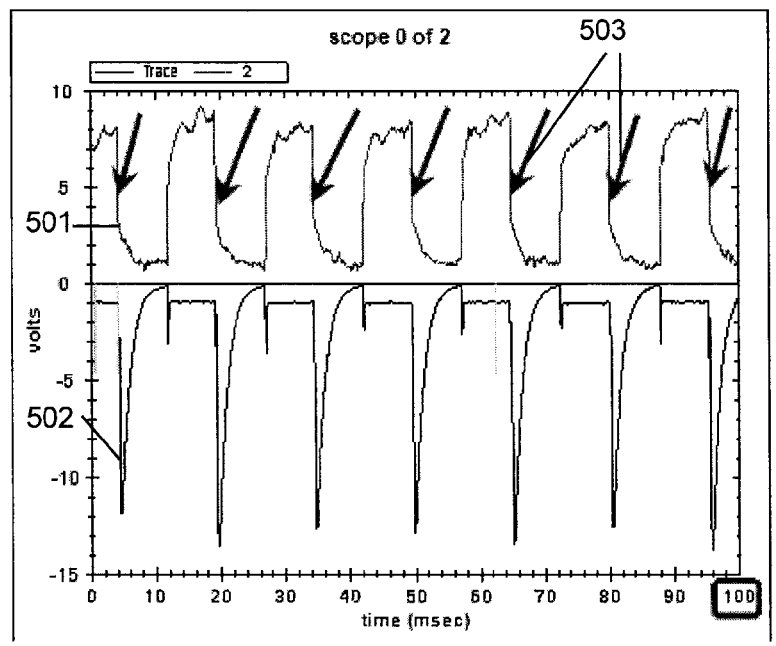
FIG. 5 is a series of output delayed fluorescence signal traces with corresponding trigger signals.

Selecting the measure LED angle box 405 causes the system to calculate an angle between the end of activation of the sample (i.e. when the sample is illuminated by the light source) and the beginning of detection of delayed fluorescence, which corresponds to the time delay between the end of illumination and the start of detection. A exemplary resulting plot of signal outputs from the light detector 102 and the light sensor 114 (FIG. 1) is shown in FIG. 5. The plot shows the trigger signal 501 and the delayed fluorescence signal 502. The end of illumination of the sample is indicated by falling edges from the trigger signal 501, indicated in FIG. 5 by arrows 503. The overall time taken for the scan is 100 ms (as set by the time base 402 shown in FIG. 4), during which time the modulator has performed six full rotations, and seven trigger signals have been detected.

To extract each trigger point, the point of maximum negative slope throughout the whole trigger signal 501 is determined. Any point having a slope within a predetermined fraction, for example 60%, of this maximum slope is accepted as a trigger point, so as to take into account variations due to noise and slowing down of the modulator.

A measure of fluorescence in the sample is determined by extracting the decay curves from the captured light signal data 502 and deriving an average output signal from the decay curves, a starting point of each decay curve being determined according to the position of a corresponding trigger signal. As detailed below, other optional steps may also be carried out on the acquired signal data.

The noise level of the signals 501, 502 will determine the limit of an acceptable scan, so these will affect the results of off-line calculations. Similarly any light leaking from the source to the detector will affect the results. If there is a light leak, this will strongly affect the noise and determine if a scan is accepted or rejected. A delay 406 (FIG. 4) may be added to shift the starting point compared with the calculated trigger point, which may be used to eliminate any rapid decaying part of the signal from the light detector, which can also strongly affect the noise. This may be used for example when analyzing data received from a separate machine, in which these parameters can be adjusted to obtain the best results given the available data. In general, however, any delay will be a fixed value given by the mechanical parameters of the system being used, and optimised for the particular set up. In a general aspect therefore, a predetermined delay may be added to each trigger signal to determine the start of each decay curve.

Figure 6:
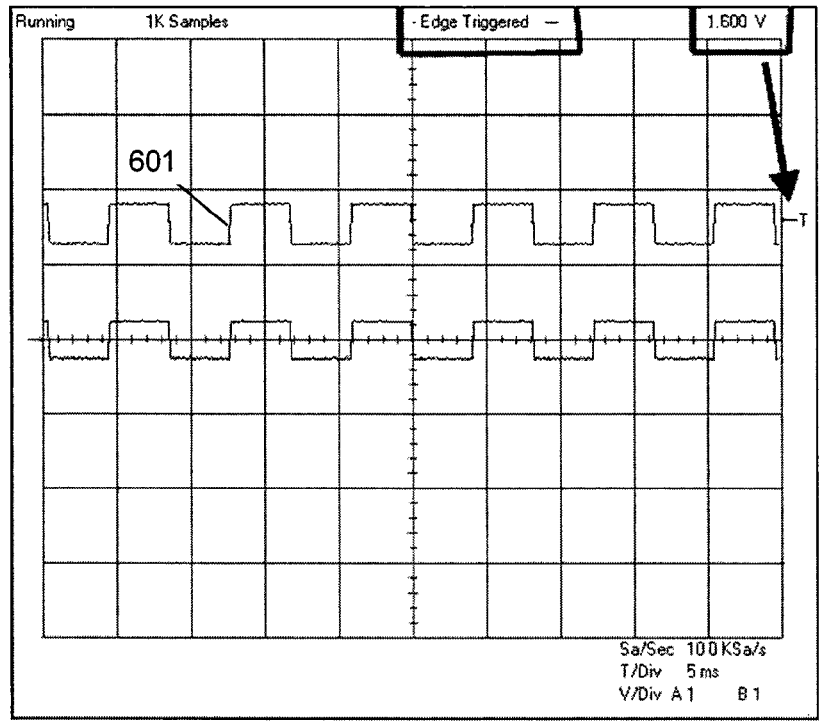
FIG. 6 is an exemplary screenshot of a computerised oscilloscope monitoring a trigger signal.

FIG. 6 shows an exemplary screen shot from the software oscilloscope, in which a trigger signal 601 is indicated. A trigger point may be selected by selecting a value between the upper and lower levels of the trigger signal, at which the maximum slope will be detected. The value may for example be the average of the upper and lower levels.

An exemplary fluorometer 100 (FIG. 1) will have two light detectors, a first detector 102 for detecting the delayed photons from the sample and a second detector 114 for detecting a trigger for timing purposes. The speed of the motor 104 turning the modulator is not assumed to be constant, but the geometry between the two plates 106, 107 of the modulator is assumed to be constant. This may be expressed as an angle between the two plates as the modulator 105 rotates to sequentially block and permit passage of photons to and from the sample 111. This angle, known as a light angle, can be measured by using the output signals from the two detectors.

A signal from the trigger detector may be always assumed to have a strong signal since the detector is in direct line of sight with the light source. The trigger signal can therefore be used as the basis for timing the light angle. The light angle can then be measured for a sample having a strong secondary emission.

Figure 7:
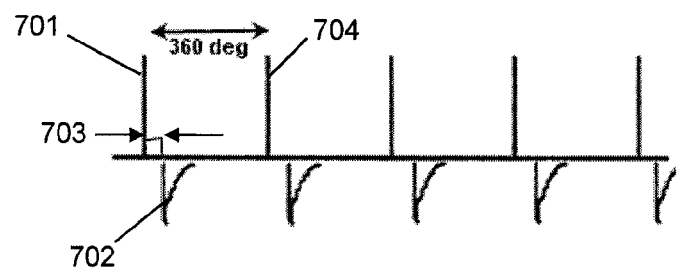
FIGS. 7 to 11 are schematic diagrams of a series of decay curves and corresponding trigger points.

The plot shown in FIG. 7 shows trigger signals 701, 704, extracted from the output of the second detector 114, and an output signal 702 from the first detector 102. In order to determine a light angle, the angular offset between each trigger signal and the output signal can be determined by measuring the distance 703 between each trigger signal and a following output signal 702 and comparing this with the distance to a subsequent trigger signal 704. Since the rotational speed is not necessarily constant, this allows the signal 702 to be adjusted accordingly when averaging multiple signals. This remains a valid method of determining the light angle, provided the relative positions of the detectors and the modulator do not change throughout a measurement cycle.

Figure 8:
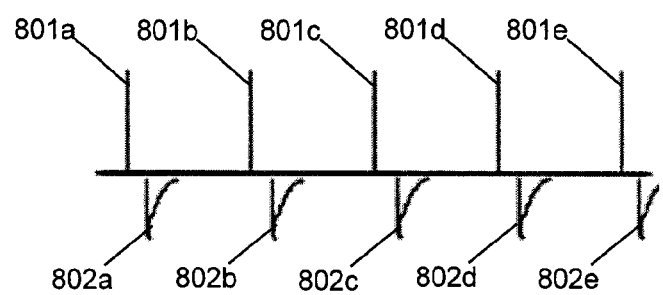

Although the trigger signal is typically a much stronger signal compared to the fluorescence signal, it too can be affected by noise. Considering first the usual case where noise is not a problem, illustrated in FIG. 8, the light angle can be readily measured for each of the pairs of trigger signals 801*a-e* and subsequent fluorescence signals 802*a-e*. The last fluorescence signal 802*e*, however, is not complete and may not therefore be appropriate for use. A decision can be made as to whether this signal 802*e* can be used by comparing the length of data remaining with a previous cycle length, i.e. between trigger signals 801*d* and 801*e*, based on the fact that the cycle length will stay approximately constant from one cycle to the next. If the amount of data is within a predetermined fraction, for example 80%, the signal 802*e* can be used. In this case, the final signal 802*e* would be rejected.

Figure 9:
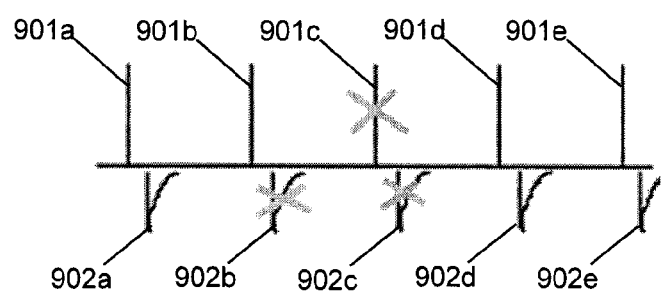

It is possible that one or more trigger signals may be missed. FIG. 9 illustrates the case where one trigger signal 901*c* is missed. This results in the need to eliminate two signals 902*b*, 902*c*, because a cycle length cannot be measured for them. To determine whether this is the case, the apparent cycle length between subsequent trigger signals 901*b*, 901*d* will be approximately twice that of the previous cycle between signals 901*a*, 901*b*. A rule can therefore be set that any cycle which is greater than a previous cycle by a set margin is eliminated from the calculations. A suitable margin would be 50%, i.e. if a cycle is greater than 150% of a previous cycle it is rejected.

Figure 10:
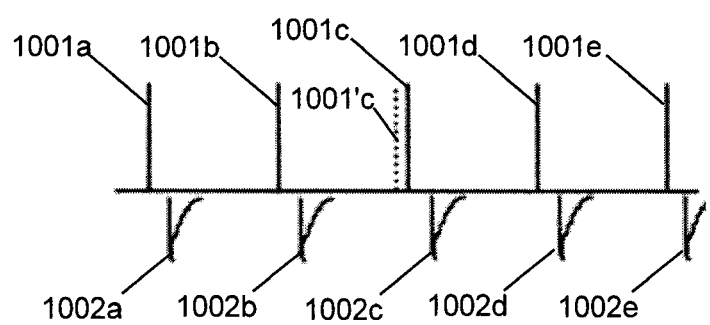

In the opposite case to that illustrated above, instead of missing a trigger signal a spurious trigger signal may be detected. This is illustrated in FIG. 10, where a spurious signal 1001'*c* is detected between trigger signals 1001*b*, 1001*c*. This spurious signal 1001'*c* would result in a shortened cycle and an incorrect offset, causing incorrect summing and averaging. This too may be detected as an anomalous cycle length. If, for example, the cycle length is less than that of the previous cycle by a set margin, for example being less than 67% of the previous cycle, the change is too great to be valid. As in the above example there is no reliable way to know which is the spurious trigger so both would be eliminated. The process can then proceed according to the previous example of a missed trigger and be treated in the same way, rejecting signals either side of the spurious trigger signal.

Figure 11:
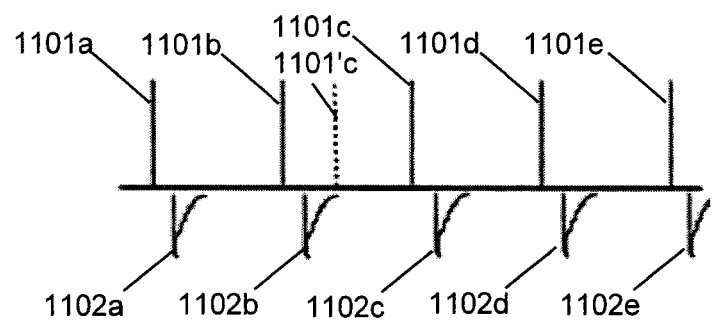

In certain cases a spurious trigger signal can be detected and eliminated without the need to eliminate any valid trigger signals. An example of this is shown in FIG. 11, in which a spurious trigger signal 1101'*c* is detected between real trigger signals 1101*b*, 1101*c*. In this case the distances between the preceding trigger signal 1101*b* and subsequent trigger signal 1101*c* are both too small to be valid. It is therefore clear which signal is spurious, and the spurious trigger signal 1101'*c* can be eliminated without affecting the remaining signals.

Once the trigger signals and cycle lengths are determined, scans of different samples are averaged together, in order to improve the signal to noise ratio of the measurement. A noise parameter may be used to determine whether a given sample is accepted or rejected, as indicated by the noise level input 407 in FIG. 4. Each signal is normalized so that its absolute value has no significance and the deviation is compared to the set noise level. The noise level of each sample is compared to the predefined noise level. Any samples not meeting the noise level are rejected, and remaining samples are averaged to obtain a final averaged sample.

Figure 12:
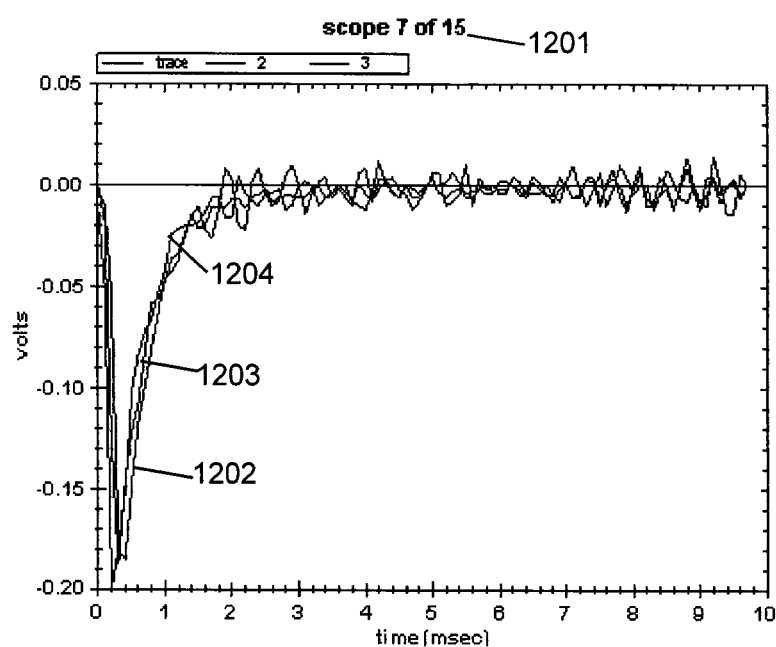
FIGS. 12 to 14 are screenshots of various output signal traces.

Once an initial average is computed, all additional samples can be inspected to see if they can be accepted or rejected. In addition to the average value, 2 other curves may be stored and illustrated, being the noisiest curve within the predefined acceptable limits, and the noisiest curve outside the acceptable limits. An example of a plot showing such results is illustrated in FIG. 12. The heading 1201 of the plot indicates that 7 out of 15 samples met the noise criterion. An average 1202 of these 7 signals is plotted, together with the noisiest acceptable signal 1203 and the noisiest unacceptable signal 1204.

Figure 13:
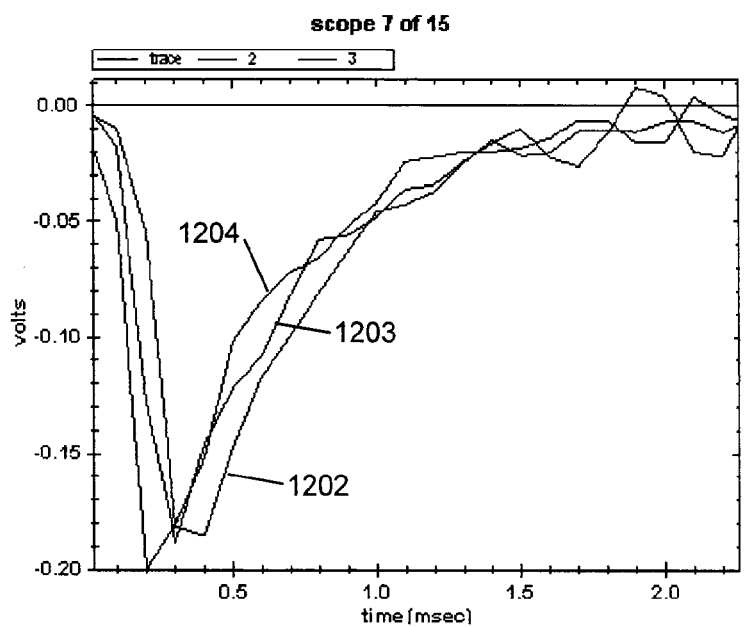

An expanded portion of the plot of FIG. 12 is shown in FIG. 13, in which the peak region is shown in more detail. Noise in the peak region is generally more significant than noise in the tail region of each curve. To compensate for this, noise in the first 20% of each curve has double weight. Noise above 30% has single weight. Between 20% and 30%, the noise factor scales between 2.0 and 1.0. In a general aspect therefore, a noise level is weighted according to the portion of the signal from light detector during each measurement cycle.

The noise level can be adjusted by altering the noise level input setting 407 (FIG. 4). The noise level is preferably based on the RMS deviation from an average curve, which allows any outlier traces to be excluded if they exceed a preset noise level. A suitable noise level may be experimentally determined from concentration curves by measuring a level that is a predetermined amount over a curve that is measured in the absence of a sample.

As shown in FIG. 13, the trigger value for the rejected signal 1204 is offset by one sampling unit in the x direction (time), given that the data is sampled every 100 microseconds. This shift caused a large deviation of the peak location compared to the other signals, which is likely to be the cause of the sample curve 1204 being rejected. The other sample data curves 1202, 1203 also show some significant deviations, but with the peak in the correct position.

Further quality control operations may be implemented, in order to ensure that the data output from the system is correct and meaningful. This can be based on a measure of the half life of the fluorescent probe being used. This should be a fixed number, and can therefore be calibrated for. This also allows signal output curves to be translated into actual concentrations, given a standard calibration curve for a known sample concentration.

Figure 14:
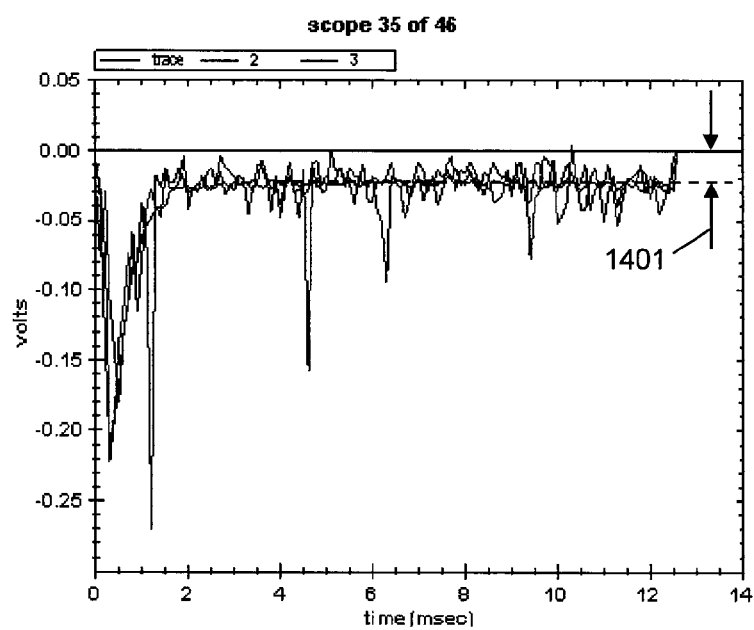

In order to obtain acceptable statistical accuracy, the area under the decay curve is preferably used to obtain a concentration. However, this assumes a decay curve having an exponential shape, and with no offset. A first correction which must therefore be carried out is to remove any DC offset in the output signal. This is illustrated in FIG. 14, in which a DC offset 1401 is clear in the raw data signal. To get an estimation of the offset, an average value of the curve counted as from a number of half lives (typically 4) to the curve end. At 4 half lives, a signal will be reduced to $\frac{1}{16}$ (or 6.25%) of its initial value. The DC offset thereby calculated can be removed from the entire sample data.

There are at least two ways by which the value of the exponential can be calculated. A first method assumes that it conforms to an exponential decay given by the specified half life. The curve is divided into 2 sections: zero to 1 half life, and 1 half life up to 4 half lives. By definition, by 1 half life the area under the curve should be half of the total area, with the other half in the remaining tail portion. In practice, the half life may not fall on one of the sample points on the curve, and integration is typically carried out only to 4 half lives and not to the end of the curve. This results in a ratio which is calculated to correct for these effects. In the ideal case the ratio of the two halves of the curve will equal 1, but in practice it is somewhat different from 1.

If we then take the ratio of the two areas and compare it to the calculated ratio, any difference should reflect an additional offset. This offset can be added so that we have a real exponential decay of the specified half life. A semi log plot of the result should then reveal a straight line. This is shown by way of example in FIG. 15, where the raw signal data 1501 has been processed to result in an output data set 1502 showing a relatively straight line. The processed curve 1502 can be equated to concentration using a calibration ratio.

A second method makes less use of an assumed exponential decay and instead assumes that the initial value of the offset obtained from the tail is correct. The area under the curve 1501 is then calculated with no further corrections.

Figure 15:
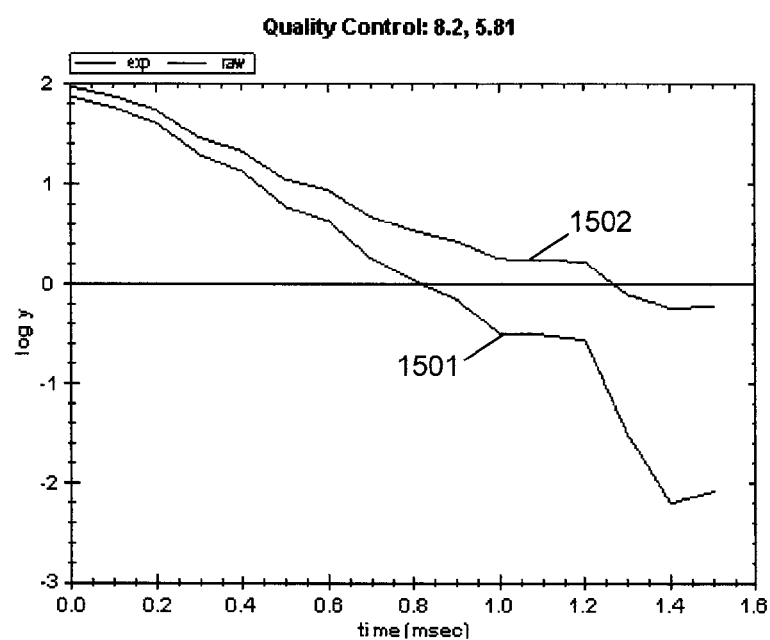
FIG. 15 is a screenshot of an output signal trace in raw and adjusted form.

The area under the curve as shown in FIG. 15 (in that case the value was 8.2) for given concentrations of probe can be presented as a standard curve, as in FIG. 17. It is preferred to use the area under the curve rather than one point value (such as peak fluorescence) as the former may be more reliable. The concentration of the probe in the sample can be derived by interpolation from the standard curve.

The measured half life of the probe may be different from the expected half life if there is any biochemical "steric hindrance", such as caused by degradation of the sample, so a comparison of the measured and expected half life may be useful. A message may be given to the operator to supply a "fresh" sample. The other possibility is that the patient has been administered some drug which will partially "bind" to the fluorescent complex and thus change the half life. As a "screen" to see if there is any "binding" the two values are compared (raw versus exponential). The two values should be within 20% of the other value. If not, there can be several iterations of the half-life to find the "altered" half-life and then report this new value (with a caveat). If the half-life can not be "found" (by the 20% agreement rule), then a message may be given to the operator reporting that this particular value is not to be trusted. Again a "fresh" sample is required.

A fluorometer may be provided in conjunction with or as a part of a machine for performing an immunoassay as illustrated in FIG. 16. A magnetic probe 1601 can move up or down and progresses laterally on a horizontal member 1602 through a linear array of various reagent wells culminating in the well containing the fluorescent probe 1603. Finally it is located at the fluorometer 1604 for fluorescence detection. To save space, the reagent wells may be provided as a circular array.

The fluorometer described herein, with or without a light detector, may also be used as part of a fluorescence microscope, since the human eye is able to see delayed fluorescence. Likewise, the fluorometer could be incorporated into a gel scanner, in which a gel is translated across the transmission path between the light source and light detector or microscope, or by using an image intensifier to analyse larger areas or the whole gel using a camera.

EXAMPLE 1

Preparation of a Stable Fluorescent Chelate 1) 2 mg pAS was dissolved in 100 μL DMSO which had been dried with molecular sieves.
2) 4 mg DTPAA was dissolved in 100 μL dried DMSO.
3) 100 uL dried Et3N was added to the product of step 2.
4) pAS prepared in step 1 was added dropwise to the DTPAA preparation of step 3 and mixed for 30 min at 20° C.
5) 4 mg poly-l-lysine was dissolved in 100 μL cacodylate buffer pH 7.0
6) The product of step 5 was added to the product of step 4 and mixed for 2 hr at 4° C.
7) 4 mg TbCl was dissolved in 100 μL 20 mM borate buffer pH 8.5.
8) The product of step 7 was added to the product of step 6 and mixed for 1 hr at 4° C.
9) NHS-Biotin was added in 100 μL DMSO to the product of step 8 and mixed for 1 hr at 4° C.
10) The product of step 9 was passed through a 0.2 μm filter.

The excitation peak of the stable fluorescent chelate is about 310 nm (UV). The emission is mainly in the green at 500 nm although there are two more peaks at 550 and 600 nm. Suitably, a PMT may collect all wavelengths from 300-700 nm. As the fluorescence is stable for a long period of time, fewer quality control tests may be needed, and with lower frequency, than with other probes. This facilitates use in a hospital setting.

EXAMPLE 2

Performing an ELISA

A typical ELISA for any particular brain specific protein is performed using the machine illustrated in FIG. 16 as follows. There is a bottle of magnetic beads (intermittent shaking) with covalently attached "capture" antibody, and 1 μL is aspirated and then transferred (using 2 servo motors) to the first reaction vial. A 5 μL sample of serum is added by the operator (using a disposable pipette). The magnetic probe moves over the first vial and moves up/down over 5 min to mix the serum plus beads. Then 100 μL of phosphate buffer is added by peristaltic pump and after mixing up/down the wash is removed from the bottom by another peristaltic "drain" pump. After two repeat buffer washes, the magnetic probe moves to the second vial. This has 1 μL of the second "detector" antibody added and is mixed up/down for 5 min, like the incubation with the previous "capture" antibody. This then also has 3 buffer washes like the previous vial. The magnetic probe then moves to the third vial which has 1 µL of the third biotinylated antibody (or the latter can be then sequentially added to the same vial). This has the same incubation and washes as the first 2 antibodies. The magnetic probe then moves to the fourth vial where 10 µL of gluteraldehyde is added to cross-link all 3 antibodies. This is mixed by up/down for 1 min and then washed 3 times with 10 µL TRIS buffer to neutralize any residual gluteraldehyde followed by 3 times more washing with buffer. The magnetic probe then moves to the fifth vial where 1 uL of avidin has been added, followed by the same mixing/washing as with the 3 previous antibodies. The magnetic probe then moves to the sixth vial where 1 µL of fluorescent chelate-linked to biotinylated polylysine is once more mixed/washed as with the prior antibody steps. Finally the magnetic probe moves into the cuvette inside the light chopper where the rotor spins for 20 seconds and the laptop controlled oscilloscope takes a reading within 20 seconds and displays the result in graphical format on the screen of the laptop. After the second and subsequent assays, all further points are displayed on the same graph to show any sequential changes in the levels of the given protein.

EXAMPLE 3

Sensitivity of Fluorometer

The stable fluorescent chelate prepared in Example 1 was serially diluted. Fluorescence measurements of this probe were made by a fluorometer according to an embodiment of the present invention and a fluorometer of the prior art (FLUOstar Optima from BMG Labtech Ltd (Bucks., UK)). The results in FIG. 17 show that there is an approximately linear relationship between fluorescence and probe concentration over three to four orders of magnitude of probe concentration for both machines. However, the fluorometer of the invention has a much greater sensitivity as shown by the steeper slope of the fluorescence curve. This makes it particularly suitable for the detection of molecules at low abundance.

Other embodiments are intentionally within the scope of the invention as defined by the appended claims.

The invention claimed is:

1. A method of detecting time-resolved fluorescence of a sample, the method comprising the steps of:
   providing a time-resolved fluorescence system having a sample holder, a motor, a light transmission modulator, a light source, and a light detector;
   disposing a sample in said sample holder;
   operating the motor to rotate said light transmission modulator;
   operating the light source to illuminate said sample when said light transmission modulator is in a first rotated position;
   stopping operation of said motor;
   capturing light signal data from said light detector indicative of the time-resolved fluorescence of said sample; and
   wherein the step of capturing light signal data is carried out after stopping operation of said motor and while said light transmission modulator is rotating.

2. The method of claim 1, further comprising the step of: detecting a rotational position of said light transmission modulator from a signal provided by a rotational detector and capturing trigger signals from said rotational detector for synchronising the captured light signal data with the rotational position of said light transmission modulator.

3. The method of claim 2, wherein a measure of the time-resolved fluorescence in said sample is determined by extracting a plurality of decay curves from said captured light signal data and deriving an average output signal from the plurality of decay curves, a starting point of each decay curve being determined according to the position of a corresponding trigger signal.

4. A computer program for instructing a computer system of a time-resolved fluorescence system to perform a method of detecting time-resolved fluorescence in a sample disposed in a sample holder of the time-resolved fluorescence system the method comprising the steps of:
   operating a motor to rotate a light transmission modulator;
   operating a light source to illuminate the sample when the light transmission modulator is in a first rotated position;
   stopping operation of the motor;
   capturing light signal data from a light detector indicative of the time-resolved fluorescence of the sample; and
   acquiring trigger signals from a light sensor configured to detect light transmission from the light source to the sample,
   wherein the steps of operating the light source and capturing light signal data are carried out after stopping operation of the motor and while the light transmission modulator is rotating.

5. The method of claim 1 wherein said sample comprises an amount of a fluorescent molecule or moiety which is indicative of an amount of a selected biological molecule present in a specimen from which said sample was taken.

6. The method of claim 5, wherein said sample is selected from the group consisting of urine, blood, serum, plasma and cerebrospinal fluid.

7. The method of claim 5, wherein said selected biological molecule is selected from the group consisting of S100 protein, a glial fibrillary acidic protein, neuron-specific enolase, a NFheavy neurofilament, NFlight neurofilament, a ubiquitin carboxyl-terminal esterase L1, a TnI troponin, a TnT troponin, a N-Terminal-pro-Brain-derived-Natriuretic-peptide, a creatine kinase MB protein, a beta 2 microglobulin, a carcinoembryonic antigen, a C reactive protein and a fibrinogen D-dimer.

8. A method of estimating an amount of a selected biological molecule present in at least one patient sample, the method comprising the steps of:
   (i) collecting the at least one patient sample, wherein said at least one patient sample is selected from the group consisting of urine, blood, serum, plasma and cerebrospinal fluid;
   (ii) contacting said at least one patient sample with a capture molecule that binds to said selected biological molecule to form a complex between said capture molecule and said selected biological molecule, thereby producing at least one test sample;
   (iii) detecting said complex by contacting and binding said complex with a probe comprising a moiety which is capable of participating in fluorescence, wherein the amount of said probe bound to said complex is indicative of the amount of said selected biological molecule present in said at least one patient sample;
   (iv) exposing said at least one test sample comprising said probe to conditions in which the fluorescence of the probe is emitted;

(v) detecting a time-resolved fluorescence in said at least one test sample; and
(vi) estimating the amount of said selected biological molecule present in said at least one patient sample from said time-resolved fluorescence detected in said at least one test sample;

wherein said detecting step comprises:
 providing a time-resolved fluorescence system having a sample holder, a motor, a light transmission modulator, a light source, and a light detector;
 disposing said at least one patient sample in said sample holder;
 operating the motor to rotate the light transmission modulator; operating the light source to illuminate said sample when the light transmission modulator is in a first rotated position;
 stopping operation of the motor;
 capturing light signal data from the light detector indicative of said time-resolved fluorescence of said sample; and
 wherein the step of capturing light signal data is carried out after stopping operation of the motor and while the light transmission modulator is rotating.

9. The method of claim 2, wherein said sample comprises an amount of a fluorescent molecule or moiety which is indicative of an amount of a selected biological molecule present in said sample.

10. The method of claim 3, wherein said sample comprises an amount of a fluorescent molecule or moiety which is indicative of an amount of a selected biological molecule present in said sample.

11. The method of claim 6, wherein said selected biological molecule is selected from the group consisting of S100 protein, a glial fibrillary acidic protein, neuron-specific enolase, a NFheavy neurofilament, NFlight neurofilament, a ubiquitin carboxyl-terminal esterase L1, a TnI troponin, a TnT troponin, a N-Terminal-pro-Brain-derived-Natriuretic-peptide, a creatine kinase MB protein, a beta 2 microglobulin, a carcinoembryonic antigen, a C reactive protein and a fibrinogen D-dimer.

* * * * *